(12) United States Patent
Takaku

(10) Patent No.: US 7,307,182 B2
(45) Date of Patent: Dec. 11, 2007

(54) 2,3-DICYANOHYDROQUINONE DERIVATIVE AND USES OF THE SAME

(75) Inventor: Koji Takaku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/519,930

(22) Filed: Sep. 13, 2006

(65) Prior Publication Data

US 2007/0057231 A1 Mar. 15, 2007

(30) Foreign Application Priority Data

Sep. 14, 2005 (JP) ............................ P2005-267035

(51) Int. Cl.
*C07C 255/50* (2006.01)
*C07C 255/51* (2006.01)

(52) U.S. Cl. ...................... 558/411; 558/303; 558/414; 428/1.1

(58) Field of Classification Search ................. 558/303, 558/411, 414; 428/1.1
See application file for complete search history.

(56) References Cited

U.S. PATENT DOCUMENTS 4,966,727 A * 10/1990 Ichihashi et al. ...... 252/299.61

5,108,651 A * 4/1992 Terashima et al. ..... 252/299.61

FOREIGN PATENT DOCUMENTS

JP 59-10557 A 1/1984

\* cited by examiner

*Primary Examiner*—Golam M. M. Shameem
(74) *Attorney, Agent, or Firm*—Birch, Stewart, Kolasch & Birch, LLP

(57) ABSTRACT

A compound represented by formula (1):

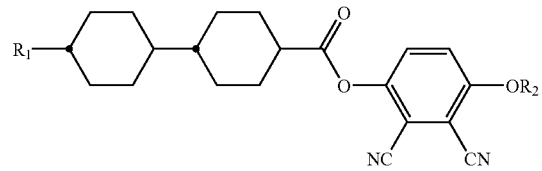

(1)

wherein $R_1$ represents an alkyl group having from 1 to 10 carbon atoms and $R_2$ represents an alkyl group having from 8 to 20 carbon atoms.

4 Claims, No Drawings

2,3-DICYANOHYDROQUINONE DERIVATIVE AND USES OF THE SAME

FIELD OF THE INVENTION

The present invention relates to a 2,3-dicyanohydroquinone derivative and uses thereof. More particularly, the invention relates to a compound which is suitable for use as a liquid-crystal compound and in a liquid-crystal composition and a display employing the composition.

BACKGROUND OF THE INVENTION

Liquid crystals (compounds) are extensively used in applications such as devices including displays and optical elements including retardation films. However, there is a desire for the development of new materials according to such purposes. A 2,3-dicycanohydroquinone derivative (trans-4-(trans-4'-alkylcyclohexyl)cyclohexanecarboxylic acid ester of a 3-alkyloxy-6-hydroxyphthalonitrile) is disclosed as a liquid-crystal material having negative permittivity anisotropy (see, for example, JP-A-59-10557). In applications such as displays including LCD's, there is a desire for the development of a liquid-crystal material superior in desired optical performance, etc. to liquid crystals heretofore in use.

SUMMARY OF THE INVENTION

An object of the invention is to provide a novel compound and uses of the compound, such as a composition, display, and optical element each containing or employing the compound. Another object of the invention is to provide a novel compound suitable for use as a liquid-crystal compound having negative permittivity anisotropy and uses of the compound.

Those objects are accomplished by the following constitutions.

(1) A compound represented by formula (1):

Formula (1):

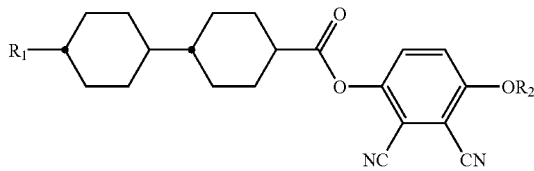

wherein $R_1$ represents an alkyl group having 1-10 carbon atoms and $R_2$ represents an alkyl group having 8-20 carbon atoms.

(2) The compound as described under (1) above wherein $R_1$ is an alkyl group having 3-5 carbon atoms and $R_2$ is an alkyl group having 8-14 carbon atoms.

(3) The compound as described under (1) above wherein $R_1$ is an alkyl group having 3-5 carbon atoms and $R_2$ is an alkyl group having 8-10 carbon atoms.

(4) A liquid-crystal composition containing at least one compound which is the compound as described under any one of (1) to (3) above.

(5) A display which comprises a pair of electrode substrates and a liquid-crystal layer disposed between the pair of electrode substrates, the liquid-crystal layer containing at least one compound which is the compound as described under any one of (1) to (3) above.

According to the invention, a compound suitable for use in applications such as displays and optical elements can be provided. Furthermore, a liquid-crystal compound having high negative permittivity anisotropy can be provided especially by using compounds having a specific structure (carbon chain length).

DETAILED DESCRIPTION OF THE INVENTION

The invention will be explained below in detail. In this specification, each "-" lying between numerals indicates the range including the numerals on both sides thereof as the minimum value and the maximum value, respectively.

The compound represented by formula (1) in the invention (often referred to as the compound of the invention) is explained.

Formula (1):

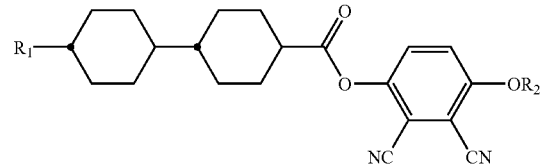

$R_1$ represents an alkyl group having 1-10 carbon atoms, and preferably represents an alkyl group having 3-5 carbon atoms (e.g., n-propyl, n-butyl, and n-pentyl). The alkyl group means a linear or branched alkyl group, and may have one or more substituents (the substituent group V shown below) or may be unsubstituted. The alkyl group may have an unsaturated bond (e.g., 3-hexenyl). Examples of the substituents include the substituent group V shown below.

(Substituent Group V)

Halogen atoms (e.g., chlorine, bromine, iodine, and fluorine), cyano, alkoxy groups having 1-10 carbon atoms, preferably 1-8 carbon atoms, more preferably 1-4 carbon atoms (e.g., methoxy, ethoxy, and 2-methoxyethoxy), acyloxy groups having 1-10 carbon atoms, preferably 2-6 carbon atoms, more preferably 2-4 carbon atoms (e.g., acetyloxy), and alkoxycarbonyl groups having 2-10 carbon atoms, preferably 2-6 carbon atoms, more preferably 2-4 carbon atoms (e.g., methoxycarbonyl and ethoxycarbonyl). These substituents may be substituted by one or more substituents selected from the substituent group V.

$R_2$ is an alkyl group having 8-20 carbon atoms, preferably 8-14 carbon atoms, more preferably 8-12 carbon atoms, even more preferably 8-10 carbon atoms (for example, n-octyl and n-decyl are preferred).

Like the $R_1$ described above, the alkyl group represented by $R_2$ means a linear or branched alkyl group, and may have one or more substituents or may be unsubstituted. It may have an unsaturated bond (e.g., 3-hexenyl).

The compound represented by formula (1) of the invention preferably is a compound in which $R_1$ is an alkyl group having 3-5 carbon atoms and $R_2$ is an alkyl group having 8-14 carbon atoms, more preferably is a compound in which $R_1$ is an alkyl group having 3-5 carbon atoms and $R_2$ is an alkyl group having 8-10 carbon atoms, and even more preferably is a compound in which $R_1$ is a group selected from n-propyl, n-butyl, and n-pentyl and $R_2$ is a group selected from n-octyl and n-decyl.

Specific examples of the compound of the invention are shown below, but the invention should not be construed as being limited to the following examples.

(1)
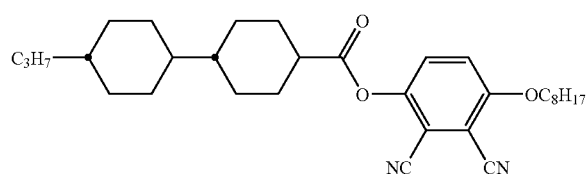

(2)
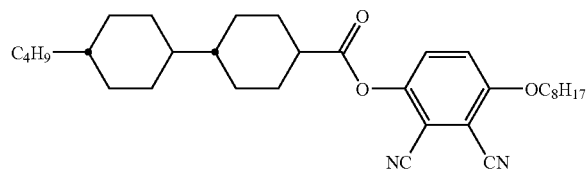

(3)
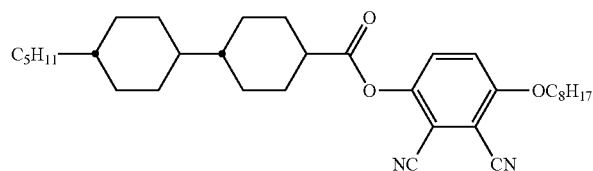

(4)
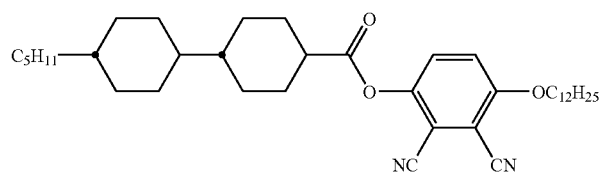

(5)
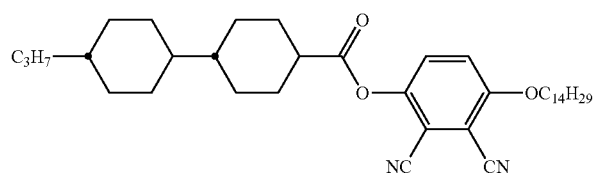

(6)
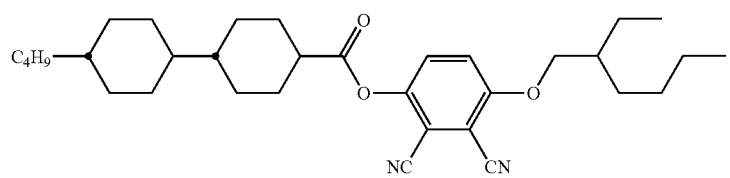

(7)
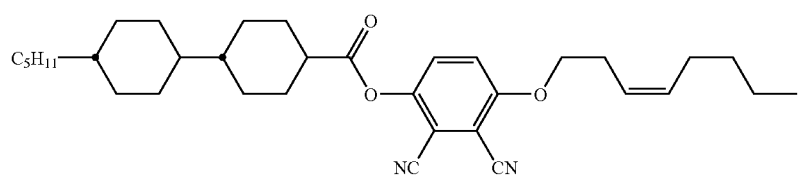

(8)
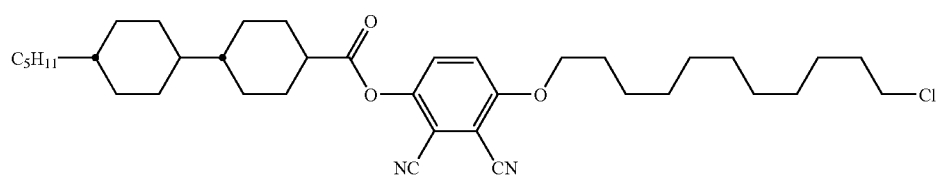

The invention provides a composition containing at least one compound represented by formula (1). This composition may contain one or more compounds represented by formula (1), and may suitably contain a known liquid-crystal compound or the like so as to be used as a liquid-crystal composition (preferably a liquid-crystal composition for guest-host use). The proportion of the compound of the invention in the composition is not particularly limited, and the compound may be mixed in any desired proportion according to desired physical properties. In the case where the composition of the invention is to be used as a liquid-crystal composition, physical properties (e.g., optical properties) of the liquid-crystal composition may be suitably regulated with the liquid crystal to be incorporated thereinto. Although liquid-crystal compounds which can be used in the composition of the invention are not limited, dual-frequency liquid crystals (nematic and smectic) are preferred. More preferred is the dual-frequency switching-mode nematic liquid crystal (H-1) described in *Applied Physics Letters*, Vol. 25, 186-188 (1974).

(H-1):

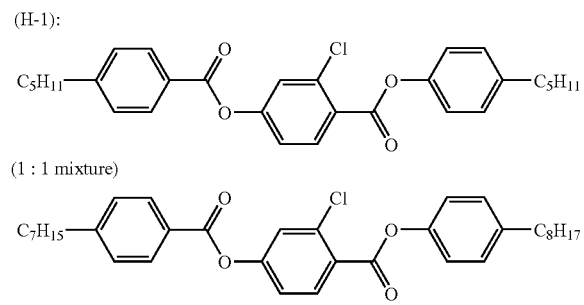

(1 : 1 mixture)

The compound and/or composition of the invention can be used in displays (e.g., liquid-crystal displays). An example of the displays comprises a pair of electrode substrates and a liquid-crystal layer disposed between the pair of electrode substrates, the liquid-crystal layer containing at least one compound which is the compound of the invention.

The compound and/or composition of the invention is suitable also for use in the optical element described below. Examples of the optical element in the invention include functional films such as circularly light-polarizing luminescent films, optical films, retardation films, ferroelectric films, antiferroelectric films, and piezoelectric films and functional elements such as (circularly) light-polarizing elements, laser oscillators utilizing optical excitation or field excitation (based on the primary protonic crystal effect), backlights for LCD's, nonlinear optical elements, electro-optic elements, pyroelectric elements, piezoelectric elements, and light modulation elements. The optical element according to the invention can be produced, for example, by (1) a method in which the compound (or composition) of the invention is applied to one substrate or a pair of substrates (as in a cell) or the like and then crosslinked or (2) a method in which the compound (or composition) is injected as it is into the space between a pair of substrates (as in a cell) or the like.

The compound of the invention can be produced according to the production processes shown in the Examples. In the production processes shown in the Examples, the target compound of the invention can be obtained by using suitably selected known starting substances having the alkyl groups represented by $R_1$ and $R_2$ of the target compound represented by formula (1). The sequence of reaction steps for substituent introduction or the like and the proportions of reactants can be suitably changed according to need.

EXAMPLES

The invention will be explained below in more detail by reference to Examples. However, these Examples are intended to illustrate the invention and the invention should not be construed as being limited to the Examples. The transition temperatures in the following Examples are given in terms of Celsius temperature.

Example 1

Synthesis of Compound (1)

Compound (1) was synthesized according to the following scheme.

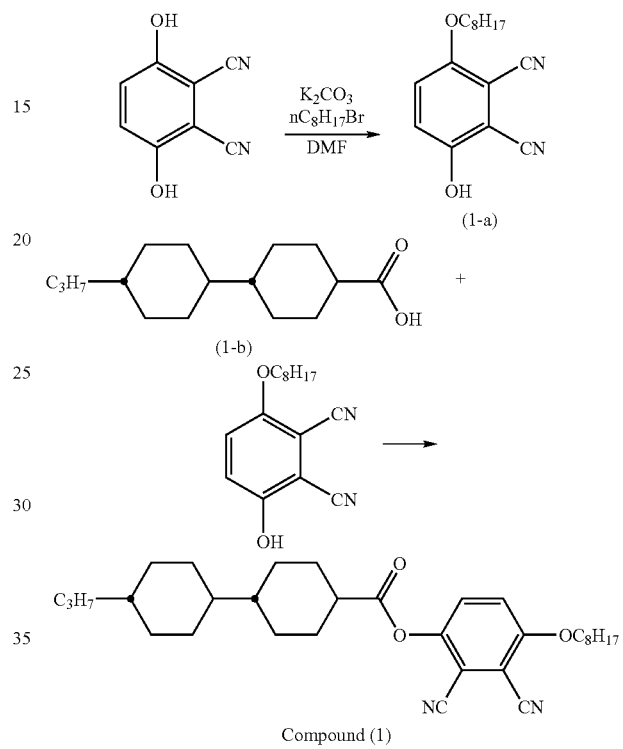

Synthesis of Compound (1-a)

Using 2,3-dicyanohydroquinone (manufactured by Wako Pure Chemical Industries, Ltd.), compound (1-a) was synthesized according to the synthesis method described in *Mol. Cryst. Liq. Cryst.*, 94, 109-118 (1983).

Synthesis of Compound (1-b)

Compound (1-b) was synthesized according to the synthesis method described in *J. Appl. Chem. USSR (Engl. Transl.)*, 59, 7, 1455-1459 (1986).

Synthesis of Liquid-Crystal Compound (1)

A methylene chloride solution (5 mL) of dicyclohexylcarbodiimide (0.9 g) was added dropwise to a methylene chloride solution (20 mL) of compound (1-b) (1 g), compound (1-a) (1.1 g), and dimethylaminopyridine (0.1 g). The resultant mixture was stirred for 1 hour with heating/refluxing. This reaction mixture was poured into ethyl acetate/1-N aqueous hydrochloric acid solution, and the organic layer was washed with 1-N aqueous hydrochloric acid solution, dried with magnesium sulfate, and then concentrated under vacuum. The concentration residue was purified by silica gel column chromatography (developing solvent: ethyl acetate/ hexane=¼). The crude crystals obtained are recrystallized from ethyl alcohol to thereby obtain liquid-crystal compound (1) (1.4 g) (the compound was identified by elemental analysis, NMR spectroscopy, and MASS spectrometry) This compound was obtained as a white solid.

The transition temperatures of the liquid-crystal compound (1) obtained were determined through an examination with a polarizing microscope (manufactured by Nikon Corp.) while changing the temperature with a hot stage (manufactured by Toyo Corp.) and through DSC.

(Transition Temperatures)
Cr 107 (unknown structure 61) SmA 188 Iso (Permittivity Anisotropy Δε)
Δε=−25.5 (calculated by extrapolation using liquid crystal ZLT-1132, manufactured by Merck & Co., Inc.)
$^1$H-NMR (CDCl$_3$)
δ: 0.74-1.2 (17H, m), 1.2-1.42 (10H, m), 1.42-1.66 (4H, m), 1.74 (4H, t), 1.8-1.97 (4H, m), 2.2 (2H, d), 2.46-2.6 (1H, m), 4.1 (2H, t), 7.18 (1H, d), 7.4 (1H, d)

Example 2

Synthesis of Liquid-Crystal Compound (2)

Liquid-crystal compound (2) was synthesized in the same manner as for liquid-crystal compound (1).

(Transition Temperatures)
Cr 95 (SmC 37 unknown structure 62) SmA 195 Iso
$^1$H-NMR (CDCl$_3$)
δ: 0.74-1.2 (17H, m), 1.2-1.43 (12H, m), 1.43-1.66 (4H, m), 1.66-1.97 (8H, m), 2.2 (2H, d), 2.47-2.61 (1H, m), 4.12 (2H, t), 7.2 (1H, d), 7.4 (1H, d)

It can be seen that the compounds of the invention show liquid crystallinity and high negative permittivity anisotropy. Since the compounds of the invention have liquid crystallinity, they can be used in displays, optical elements, etc. In particular, the compounds are suitable for use as liquid-crystal compounds having negative permittivity anisotropy in applications such as displays.

This application is based on Japanese Patent application JP 2005-267035, filed Sep. 14, 2005, the entire content of which is hereby incorporated by reference, the same as if set forth at length.

What is claimed is:

1. A compound represented by formula (1):

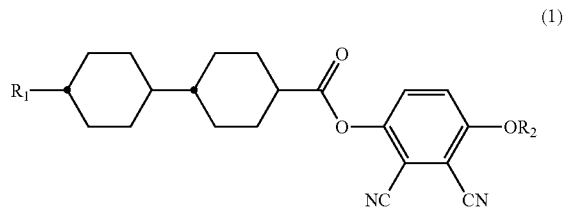

wherein $R_1$ represents an alkyl group having from 1 to 10 carbon atoms and $R_2$ represents an alkyl group having from 8 to 20 carbon atoms.

2. The compound as claimed in claim 1, wherein $R_1$ represents an alkyl group having from 3 to 5 carbon atoms and $R_2$ represents an alkyl group having from 8 to 14 carbon atoms.

3. The compound as claimed in claim 1, wherein $R_1$ represents an alkyl group having from 3 to 5 carbon atoms and $R_2$ represents an alkyl group having from 8 to 10 carbon atoms.

4. A display which comprises a pair of electrode substrates and a liquid-crystal layer provided between the pair of electrode substrates, the liquid-crystal layer containing the compound as claimed in claim 1.

* * * * *